United States Patent [19]

Stemmler

[11] Patent Number: 4,642,150
[45] Date of Patent: Feb. 10, 1987

[54] METHOD AND APPARATUS FOR SECURING ELASTIC TAPES TO A MATERIAL WEB

[75] Inventor: Kurt Stemmler, Neuwied, Fed. Rep. of Germany

[73] Assignee: Winkler+Duennebier Maschinenfabrik+Eisengiesserei GmbH & Co. KG., Neuwied, Fed. Rep. of Germany

[21] Appl. No.: 801,138

[22] Filed: Nov. 22, 1985

[30] Foreign Application Priority Data

Dec. 5, 1984 [DE] Fed. Rep. of Germany ....... 3444331

[51] Int. Cl.⁴ ............................................. B32B 31/08
[52] U.S. Cl. .................................... 156/164; 156/229; 156/265; 156/285; 156/495; 156/497; 156/519; 156/520; 156/556; 156/560
[58] Field of Search ............... 156/163, 164, 229, 265, 156/285, 495, 497, 519, 520, 556, 560

[56] References Cited

U.S. PATENT DOCUMENTS

| | | | |
|---|---|---|---|
| 3,957,570 | 5/1976 | Helm | 156/519 |
| 4,259,220 | 3/1981 | Bunnelle et al. | 525/98 |
| 4,297,157 | 10/1981 | Van Vliet | 156/164 |
| 4,413,623 | 11/1983 | Pieniak | 156/229 |
| 4,448,631 | 5/1984 | Eaton et al. | 156/556 |
| 4,479,836 | 10/1984 | Dickover et al. | 156/164 |
| 4,572,043 | 2/1986 | Bianco | 156/164 |
| 4,574,022 | 3/1986 | Johnson et al. | 156/164 |
| 4,578,133 | 3/1986 | Oshefsky et al. | 156/164 |

FOREIGN PATENT DOCUMENTS 2649948  5/1977  Fed. Rep. of Germany .

Primary Examiner—Jerome Massie
Attorney, Agent, or Firm—W. G. Fasse; D. H. Kane, Jr.

[57] ABSTRACT

Uniform lengths of elastic tape are secured to a continuously advancing material web, for example, to make baby diapers. First an intermittently advancing tape is repeatedly gathered, for example, by laying tape sections into a depression of defined dimensions, to relieve the tape sections of any stretching. This assures tape sections of uniform length which are then stretched, cut and applied to the material web, for example, by an adhesive bonding. The apparatus used for performing these steps has several cooperating rollers of which the first has the depressions in its surface and is rotated intermittently while the second roller is rotated continuously. The spacings between neighboring tape sections bonded to the web preferably have a uniform length.

15 Claims, 6 Drawing Figures

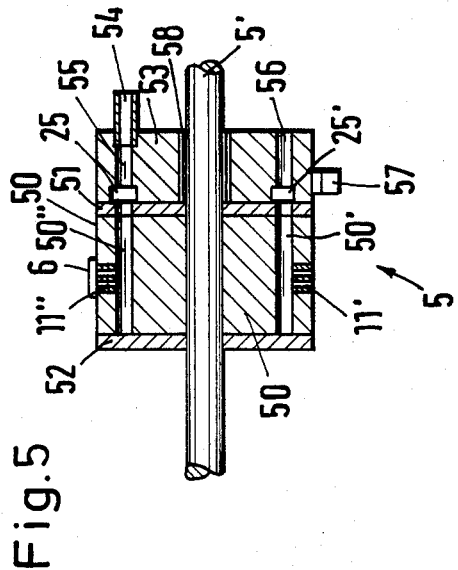

METHOD AND APPARATUS FOR SECURING ELASTIC TAPES TO A MATERIAL WEB

FIELD OF THE INVENTION

The invention relates to a method and apparatus for securing elastic tapes to a web of material, especially a so-called "endless" web moving continuously, for example, for manufacturing baby diapers, including disposable diapers and other personal care articles of different types. The elastic tapes are to be applied, especially to diaper cut-outs through which the baby's legs pass. Further, these tapes, such as rubber bands, must be so applied to the web around the cut-outs that a proper fit around the baby's leg is assured.

DESCRIPTION OF THE PRIOR ART

German Patent Publication (DE-OS) No. 2,649,948 discloses a method and apparatus suitable for the above mentioned purposes. According to this prior art the different materials, namely the web and the elastic tapes, are withdrawn as endless webs and tapes from supply rollers which feed the materials into the manufacturing machine. Thus, a continuous, uninterrupted belt of diapers is initially made which is severed into individual pieces substantially at the end of the manufacturing steps. After the pieces have been severed from the continuous belt, the pieces are folded and supplied to an automatic packaging machine.

The elastic tapes around the leg openings must provide a certain tight fit so that the diaper may serve its intended purpose. On the other hand, it is desirable that the outer surface of the material forming the diaper is substantially free of wrinkles and folds. The sufficiently tight fit around the legs and the substantially wrinkle-free appearance of the remainder of the diaper are two requirements which are not necessarily compatible with each other, especially when the material of which the diapers are made is an essentially non-elastic film or the like. Thus, it is necessary that the elastic tapes are either applied in a nonstretched state to a gathered or folded web material, or the other possibility involves applying the elastic tape in a stretched out state to a smooth, non-wrinkled web resting on a support. The web is usually a film of plastics material.

The first possibility of applying the tape in an unstretched state to a folded film is employed in U.S. Pat. No. 4,259,220 (Bunnelle et al). The apparatus used in this U.S. patent requires a substantial and involved apparatus for the gathering or folding of the film. Such expensive and involved apparatus is not justified as far as manufacturing costs are concerned.

The second possibility of applying a stretched elastic tape to a smooth piece of film is employed in German Patent Publication (DE-OS) No. 2,649,948 which requires a smaller technical effort and expense for applying the elastic tapes in pairs and in an endless manner to the film in the running direction, whereby the elastic tapes are stretched prior to their adhesive bonding to the film.

The above mentioned German Patent Publication (DE-OS) No. 2,649,948 discloses panty type of diapers in which the elastic tapes are continuously applied to the continuous material web which has not yet been cut into pieces. However, the elastic tapes are adhesively bonded to the cover film of the diaper only in the zone around the leg openings or cut-outs. The elastic fit is needed only in this area and actually would be disturbing in any other portion of the panty type diaper. However, according to this prior art the endless, prestretched elastic tapes reach over the entire length of the individual diaper and are severed only at the time of cutting the multi-layer web into pieces. As a result, the end portions of the elastic tapes, which are not glued in place, project from the diaper material web and have no purpose, whereby a substantial waste of elastic tape is involved. In fact, these tape ends, which are not glued in place, may even impair the further manufacturing steps and could even result in manufacturing faults. The just mentioned waste of elastic tape is rather substantial since the nonglued ends constitute a large percentage of the tape length needed for the intended elastic fit.

Another disadvantage of the prior art as represented by the German Patent Publication (DE-OS) No. 2,649,948 resides in the fact that the two elastic tapes which are to be adhesively bonded to the moving material web are applied with different stretching or biasing forces in the zones where they are glued to the material web. The roller pair which is used for stretching the two elastic tapes stretches both tapes to the same lengths. However, due to the inhomogeneity and due to measurement tolerances within the individual tape, it is quite possible that the tension varies from tape to tape. This undesirable effect is further amplified due to the fact that the biasing force is applied to endless, elastic tapes, whereby differences in the tensioning may accumulate from work step to work step. This fact impairs the application of the required glue or adhesive which must be applied to zones of the tapes while they are under tension and which must be applied intermittently to both tapes simultaneously at the respectively same locations. This requirement is difficult to meet because when the elastic tapes, or rather the zones of these tapes to which the adhesive has been applied, are brought into contact with the material web, it is possible that the zones with the adhesive of the two tapes are displaced relative to each other due to the different tensions in the two tapes. Thus, the elastic tapes are also displaced relative to the leg openings in the material web. The undesirable result of these difficulties is a diaper that does not fit properly at least in the zone of the leg openings. Even worse, complete rejects may result and the operation of the packaging machine may be impaired. Such impairment is due to the fact that the elastic tapes, after they have been severed together with the material web, contract again and due to their different tensionings and due to their displacement relative to each other, cause a gathering or folding around the leg openings which differs from one opening to the other. As a result, it is difficult to mechanically fold the diapers in a cross direction and in a longitudinal direction, which in turn makes it difficult to place the diapers in a carton.

OBJECTS OF THE INVENTION

In view of the foregoing it is the aim of the invention to achieve the following objects singly or in combination:

to provide a method and apparatus of the type described above which avoids the enumerated disadvantages of the prior art;

to make sure that the elastic tape sections have only that length which is necessary for the intended purpose of providing a proper, elastic fit around the leg openings; and to avoid the stretching of an entire elastic tape by making sure that only an individual length of tape is being stretched for the intended purpose.

SUMMARY OF THE INVENTION

The above objectives have been achieved according to the invention in that the endless, elastic tape is first gathered or folded along a predetermined length, whereupon this predetermined length is stretched and cut before the severed elastic tape section is applied in a stretched condition and with a spacing from the previously applied tape section, to the material web, for example, by an adhesive bonding. The end or tail of a tape section is temporarily held or clamped down during the gathering and stretching.

Thus, the length of each elastic tape section is first defined when that portion of the tape is in a completely, or at least substantially completely tension-free condition. This condition is achieved by the so-called gathering or folding which may involve forming a loop of tape or a curved tape portion, whereupon the loop or curved portion itself is stretched and cut when it is under tension. Thus, it is made sure that the tape section in its stretched condition has an exactly defined rated or required length. As a result it has only the length needed for elastically surrounding the leg opening, whereby waste is avoided. The tape section is applied in its stretched condition to the endless material web or film, whereby the spacings between neighboring tape sections along the web are of uniform length and any free ends of elastic tape are avoided.

The apparatus for performing the just described method comprises a first elastic tape supply roller located upstream of a stretching and applicator roller as viewed in the feed advance direction. The supply roller is rotating in a discontinuous, intermittent manner and has depressions in its surface. A tape portion is laid into these depressions while it is still being held to the surface of the supply roller, but without stretching. The supply roller is further equipped with countering bars for cooperation with cutting knives which are carried by the stretching and applicator second roller. The second roller is also equipped with holding members for the severed tape sections and the first roller has holding elements for the elastic tape. The holding elements and members preferably operate as suction devices.

Preferably, the supply roller cooperates with a third roller for assuring the feeding of a predetermined length to the supply roller in each intermittent step of the supply roller and to further make sure that the predetermined lengths of elastic tape are properly "gathered" or folded into the depressions of the surface of the supply roller. Preferably, the third roller has a segmented surface.

BRIEF DESCRIPTION OF THE DRAWINGS

In order that the invention may be clearly understood, it will now be described, by way of example, with reference to the accompanying drawings, wherein:

FIG. 4 shows a sectional view along section line 4—4 in FIG. 2;

FIG. 5 is a sectional view along section line 5—5 in FIG. 2; and

FIG. 6 is a sectional view along section line 6—6 in FIG. 2.

DETAILED DESCRIPTION OF PREFERRED EXAMPLE EMBODIMENTS AND OF THE BEST MODE OF THE INVENTION

Figure 1:
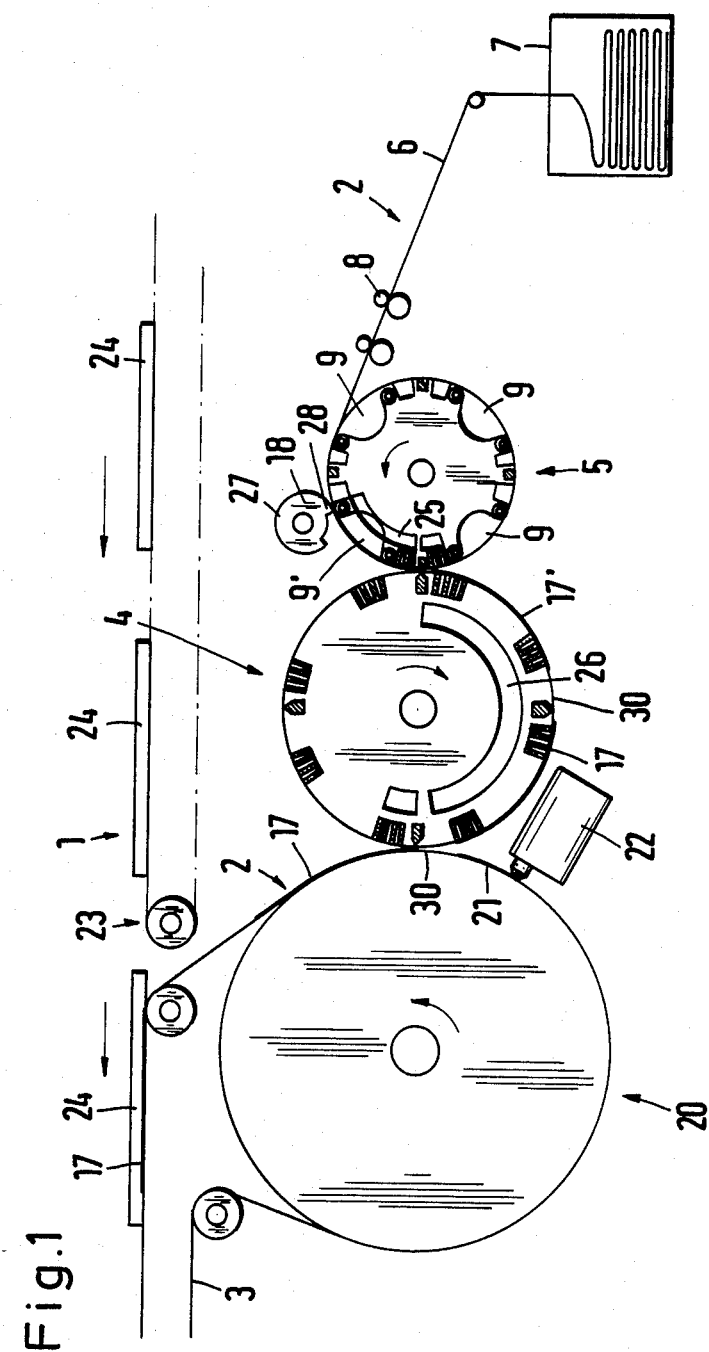
FIG. 1 is a schematic side view of an apparatus according to the invention comprising the features needed for performing the method according to the invention.
Figure 2:
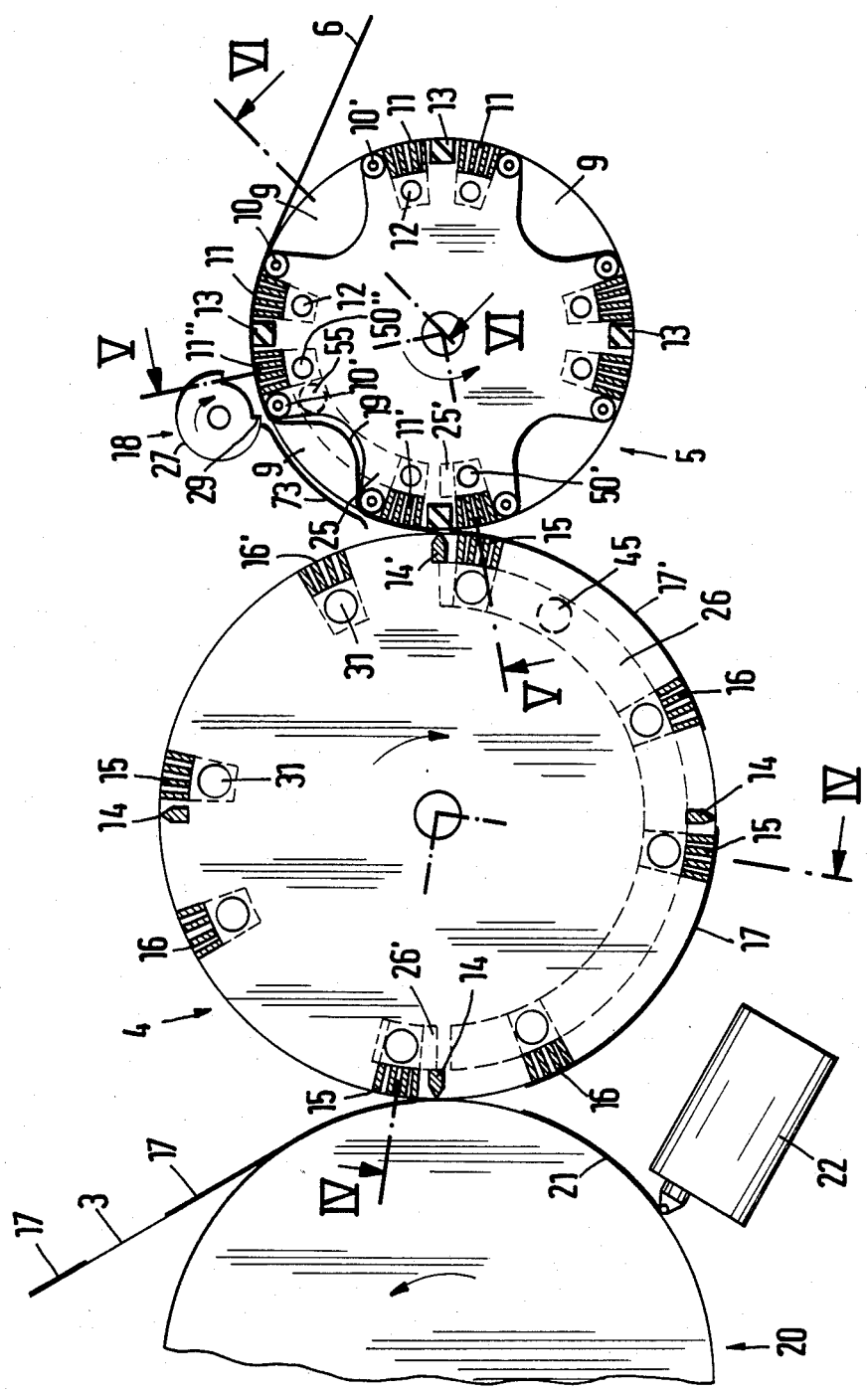
FIG. 2 shows a view similar to that of FIG. 1 on an enlarged scale for illustrating the details of the first elastic tape supply roller and of the second stretching and applicator roller.

Referring to FIGS. 1 and 2 the apparatus 1 according to the invention for securing elastic taper material 2 to a continuously moving material web 3 comprises two primary rollers. The first elastic tape supply roller 5 is arranged upstream, as viewed in the feed advance direction, of the second stretching and applicator roller 4. The first roller is driven in a discontinuous, intermittent manner. The second roller is continuously driven. The elastic tape material 2 is fed to the supply roller 5 as an endless elastic tape 6 from a supply bin 7, for example, with the aid of transport rollers 8. The first supply roller 5 is equipped in its surface with several depressions 9 for gathering or folding sections of elastic tape 6 into these depressions.

A pair of slide rollers 10, 10' is arranged in the surface of the roller 5 alongside each edge of the respective depression 9. Thus, these slide rollers are located in the transition zone between the roller or cylinder surface or jacket of the supply roller 5 and the respective depression 9. Further, the supply roller 5 is equipped with a plurality of elongated rods 11 forming holding elements for the respective tape section. These rods or holding elements 11 are provided with suction holes connected to a suction duct 12 which in turn is connected to a vacuum pump not shown. Countering bars 13 are located in the surface of the roller 5 between two holding rods or elements 11. These countering bars 13 cooperate with cutting knives 14 located in the surface or jacket of the stretching and applicator roller 4 forming the second roller.

The second roller 4 is also equipped with holding members 15, 16 of the same construction as the holding elements 11 described above, in the first roller 5. The holding members 15, 16, are arranged in pairs relative to a respective cutting knife 14. A first holding member is located close to the respective knife, whereas a second holding member is located further away from the respective knife as viewed in the rotating direction indicated by the respective arrow in the roller 4. Stated differently, the two holding members 15, 16 of a pair are arranged ahead of the respective cutting knife 14 as viewed in the rotational direction. Thus, the two holding members 15, 16 of a pair together carry or hold a tape section 17 at the time when that tape section is to be severed by the cutting knife 14 from the endless elastic tape 6.

The supply roller 5 cooperates with a third pulling roller 18 which is preferably constructed with a roller jacket having a segmented surface. The pulling roller 18 with its segmented surface pulls predetermined lengths of tape onto the supply roller 5 and makes sure that these lengths of tape are gathered or folded into the depressions 9.

The supply roller 5 with its segmented pulling roller 18 and the stretching and applicator roller 4 operate as follows. The roller 4 runs with a constant r.p.m. continuously, whereby the cutting knife 14, 14' is moved with a uniform speed and without any interruptions past the supply roller 5. During the cutting operation the circumferential speeds of the first roller 5 and of the second roller 4 are equal to each other. As soon as the cutting knife 14' has severed the tape section 17', the r.p.m. of the supply roller 5 is quickly reduced to zero. The pulling, segmented roller 18 runs preferably continuously for feeding the tape resting on the larger radius surface 27 of the pulling roller 18 into the next available depression 9' while the supply roller 5 is stationary. FIG. 2 shows how the next tape section 19 is gathered or folded into the depression 9'. It is not necessary that the elastic tape section 19 completely hugs the surface of the depression 9 or 9'. It is sufficient to just gather or fold the tape material into the depression to achieve the desired removal of all tensions from the respective tape section. As soon as the elastic tape section 19 rests in the respective depression, the supply roller 5 is started up again and accelerated until its circumferential speed is equal to the circumferential speed of the second roller 4. Additonally, when the two circumferential speeds are equal to each other, the holding element 11' of the supply roller 5 faces directly the holding member 16' of the second roller 4.

The holding element 11' thus can transfer the leading end of the tape section 19 to the holding member 16' of the second roller 4 by a proper control of the respective suctions.

As soon as the transfer of the leading end of the tape section 19 is completed, the speed of the first roller 5 is reduced, whereby the tape section 19 is pulled out of the depression 9' and stretched by the movement of the second roller 4. Thereafter, the speed of the supply roller 5 is increased until it reaches the same circumferential speed as the second roller 4, whereby the next holding element 11' behind the depression 9, as viewed in the rotational direction of the roller 5, comes into a position for cooperation with the holding member 15 of the roller 4 just ahead of the cutting knife 14. As the rotation continues, the trailing end of the tape section 19 is transferred from the holding element 11" to the holding member 15. Shortly thereafter, the tape section 19 is severed by the knife 14 and the tape section 19 is now completely held by the roller 4. The tape section 17' illustrates this situation in FIG. 2.

As the second roller 2 keeps rotating, it transports the tape sections 17, 17' to the material web 3 travelling around a fourth roller 20. An adhesive supply device 22 of conventional construction has in the meantime applied a length of adhesive 21 to the material web 3. As soon as the tape section 17 contacts the adhesive 21 on the web 3 under pressure exerted between the second roller 4 and the fourth roller 20, the leading holding member 16 releases the leading end of the tape section 17, whereby the web 3 entrains the tape section 17 for transport toward a conveyor 23 supplying moisture absorbing elements 24, such as cotton flake pads or the like. These pads 24 travel onto the web 3 provided with adhesive 21 and tape sections 17, 17'. A simple belt conveyor is suitable for the purposes of the conveyor 23. Preferably, the speed of the web 3 and of the conveyor 23 is so coordinated that the pads 24 are aligned or in register with the tape sections 17 to assure a symmetric arrangement between the tape sections 17 and a cut-out provided in the respective pad 24, for example, in the form of a leg opening. The pad 24 is preferably longer than the elastic tape section 17 so as to cover the ends of the tape section 17.

It is possible that several elastic tapes 6 are supplied in parallel with an apparatus as described above if two parallel tape sections 17 are desired, for example, in an article of personal care, such as a diaper. The actual length of the respective rollers would be so as to accommodate at least two or even more parallel elastic tapes. Thus, an apparatus according to the invention makes it possible to supply tape sections 17 in a precisely defined length and with uniform spacings from each other to an endless web 3 and to bond these elastic tape sections to the web 3, for example, by an adhesive bond. This is achieved by the intermittent operation of the supply roller 5 which provides with its depression 9 a tape supply of defined length while that length is not stretched. Thereafter, the respective length is stretched without stretching the entire elastic tape due to the operation of the roller 18. Only the stretched section is then severed. Incidentally, the invention is not limited to the curved cross-section of the depression 9 in the surface of the roller 5. Other suitable cross-sections for the depressions 9 are possible. It is merely essential that the supply roller 5 cooperates in the described manner with the stretching and applicator roller 4. Due to the depressions 9, 9' in the first roller 5, the first roller can have a smaller diameter than the second roller 4. In summary, the first roller 5 serves for the "gathering" of the tape sections and the section roller 4 stretches these sections individually and independently of the entire length of the elastic tape or tapes 6.

The control of the suction openings in the holding elements 11 of the roller 5 and the holding members 15, 16 of the roller 4 is accomplished by known means, whereby suctions ducts 12, 31 and additional control channels 25, 26 connect the respective suction openings to a vacuum source as mentioned.

The segmented roller 18 can be replaced by a liftable cylindrical roller which, just as the segmented roller 18, functions for a predetermined length of time as a friction or pressure roller to feed an elastic tape section 19 into the depression 9' as described. As soon as this feeding is completed, the contact between the segmented roller 18 or a liftable cylindrical roller and the elastic tape 6 is interrupted. More specifically, the contact between the roller 18 and the sliding roller 10, 10' is interrupted or the cylindrical roller is lifted off the sliding roller 10.

Incidentally, FIG. 1 shows the segmented roller 18 at the beginning of its work stroke or step when the leading edge 28 of its large diameter circumference 27 is located just ahead of a recess 9'. On the other hand, in FIG. 2 the illustrated position of the segmented roller 18 shows the latter at the end of its work stroke when its trailing edge 29 of its large diameter circumference 27 contacts the sliding roller 10. The circumference 27 of the large diameter of the segmented roller 18 corresponds to the length of the tape section 19 that is being fed into the recess 9 while the supply roller 5 does not rotate.

Due to the repeated stopping of the supply roller 5, a spacing 30 is provided between neighboring tape sections 17 on the roller 4. This spacing is also due to the distance between the rear holding member 15 of a leading tape section 15 and the leading holding member 16 for the trailing tape section 17', please see FIG. 2.

FIG. 2 also shows a guide plate 73 for making sure that the tape section 19 to be severed slides into the recess 9'. As mentioned, it is not necessary that the tape section 19 completely hugs the contour of the depression 9' as long as the tape section is free of any stretching when it is being gathered in the depression 9'.

Figure 3:
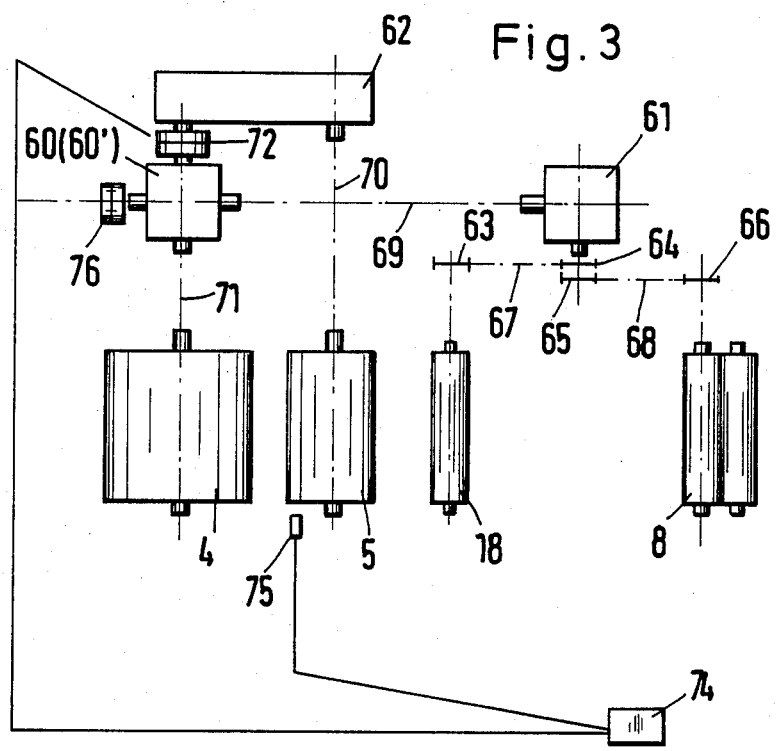
FIG. 3 is a schematic illustration of the drive mechanism for the several rollers of the apparatus according to the invention.

FIG. 3 illustrates the various drive means for the several rollers. All drive power is derived from a main drive motor, not shown. A single step or on-off clutch 76 is connected between the main drive motor a miter type gear box 60, 60'. The second roller 4 is connected through a clutch 71 to the angular gear box 60, 60'. The supply roller 5 is driven intermittently through an electro-magnetic clutch 72 and through a stepping gear drive 62 connected, for example, by a universal joint shaft 70 to the roller 5. A universal joint shaft 69 connects an angular gear box 61 to the miter gear 60, 60'. The gear 61 in turn drives a pair of feed advance rollers 8, also shown in FIG. 1, through a gear pulley 65 and a toothed belt 68 running around a further gear pulley 66. The gear 61 further drives the pulling roller 18 through gear pulleys 63, 64 interconnected by a gear belt 67.

A sensor device 75 which, for example, monitors whether the roller 5 rotates or has stopped, provides a respective signal to a control unit 74 which in turn controls the clutches 72 and 76 for a precise positioning of the first supply roller 5 to make sure that the slide rollers 10 are properly aligned with the segmented pulling roller 18. The drive for the roller 5 is derived from the drive for the roller 4 through the clutch 72 and the stepping gear drive 62 which guarantees the required synchronism between the rollers 4 and 5 at the time of the operation of the cutting knives 14. Incidentally, each of the rollers shown in FIG. 3 is adjustable in its spacing relative to the respective roller with which it cooperates. Such roller adjustment means are conventional and hence not shown. If necessary, the miter type gear 60 may include a differential gear section 60' for adjusting the timing between the tape supply system of the invention and the remaining components of the manufacturing machine including the conveyor 23.

FIG. 4 illustrates the suction supply for the roller 4. A body 40 forming the roller 4 is supported on a shaft 4'. A control valve 43 is movably supported at one end of the roller body 40 on the shaft 4' by a bearing 48. In operation the shaft 4' and the roller body 40 rotate while the control valve 43 is held stationary by a stop member 47. The roller body 40 comprises longitudinal bores 40' and 40" each of which is closed by a stopper 41 at the left-hand end of the body 40 opposite the control valve 43. The bores 40' and 40" are opened toward the valve 43.

The longitudinal bores 40' and 40" communicate with the suction holes in the holding members 15, 16 to suck a tape section 17, 17' against the surface of the roller 4. The control valve 43 comprises the above mentioned control duct or ring channel 26 and a further duct 26'. The ring duct or channel 26 is connected through a bore 45 and a suction air inlet 44 with the suction pump, not shown. The duct 26' is also a ring channel connected through a bore 46 to the atmosphere for venting. In operation, the body 40 of the roller 4 rotates with its bores 40', 40" once along the ring channels 26, 26' during each rotation, whereby the bores 40' and 40" are first connected to the vacuum pump and then to the atmosphere and so on.

FIG. 5 shows the vacuum supply for the first roller 5. The roller body 50 is mounted on a shaft 5'. A disk 51, 52 is secured to the body 50 at each end. The disks are also supported on the shaft 5' concentrically with the body 50 which comprises longitudinal bores 50', 50", one end of which is closed by the disk 52 while the other end of these longitudinal bores registers with respective holes in the disk 51 for connection to the control valve 53. The longitudinal bores 50', 50" communicate with the suction holes in the holding elements 11', 11" for holding the tape 6 against the surface of the roller 5.

In operation, the shaft 5' rotates the roller body 50 with its disks 51, 52 while the control valve 53 remains stationary relative to the shaft 5' with the aid of the bearing 58 and with the aid of the stop member 57. Here again, the control valve 53 comprises the above mentioned control duct 25 and a further control duct 25'. These ducts 25, 25' form ring channels, whereby the ring channel 25 communicates through the suction inlet 54 with a suction source, not shown, while the control channel communicates through a bore 56 with the atmosphere. As the roller body 50 rotates, the bores 50', 50" pass with their open ends once for each rotation along the ring channels 25, 25' for sequential connection to the reduced pressure or vacuum and to the atmosphere.

FIG. 6 shows the arrangement of the slide rollers 10 alongside an edge of the respective depressions 9. The slide rollers are supported for rotation in the disks 51, 52.

Although the invention has been described with reference to specific example embodiments, it will be appreciated, that it is intended to cover all modifications and equivalents within the scope of the appended claims.

What I claim is:

1. A method for securing a determined length of an elastic tape to a material web, comprising the following steps:
   (a) continuously advancing said material web,
   (b) discontinuously advancing said elastic tape and intermittently gathering sections of said elastic tape to substantially free the tape sections from any stretching force to assure a uniform length for each section,
   (c) sequentially stretching said gathered tape sections,
   (d) cutting off said stretched tape sections, and
   (e) sequentially bonding cut-off tape sections to said advancing material web at substantially uniform spacings between neighboring tape sections bonded to said material web.

2. The method of claim 1, wherein said cut-off tape sections are adhesively bonded to said material web.

3. The method of claim 2, wherein said gathering step is performed by laying each tape section into a curved shape.

4. An apparatus for securing a determined length of an elastic tape to a material web, comprising:
   (a) means for continuously advancing said material web,
   (b) first tape supply roller means (5) for discontinuously advancing said elastic tape (6), said first roller means having a surface with curved depressions (9) in said surface for intermittently gathering sections of said elastic tape into said depressions (9) to substantially free said sections from any stretching force to assure a uniform length for each section,
   (c) second continuously rotating stretching roller means (4) arranged for cooperation with said first roller means for sequentially stretching said gathered tape sections, (d) cutting means arranged for cutting off a stretched tape section, and
(e) means for sequentially transferring and bonding cut-off tape sections to said advancing material web at substantially uniform spacings between neighboring tape sections bonded to said material web.

5. The apparatus of claim 4, comprising third roller means (18) arranged for cooperation with said first roller means for assisting in said gathering of elastic tape sections into said depressions.

6. The apparatus of claim 5, wherein said third roller means (18) comprise a segmented surface.

7. The apparatus of claim 5, wherein said first roller means (5) comprise slide rollers (10, 10') arranged in said first roller means alongside an edge of said depressions for cooperation with said third roller means in laying each tape section into a curved shape in the respective depression (9).

8. The apparatus of claim 7, wherein one slide roller is located along each edge of each depression, said slide rollers operating as counter rollers for said third rollers.

9. The apparatus of claim 4, wherein said first roller means comprise a roller surface and countering bars arranged in said roller surface, said cutting means comprising cutting knives arranged in said second roller means for cooperation with said countering bars in said first roller means.

10. The apparatus of claim 4, wherein said first roller means comprises holding elements (11) in its surface, said holding elements being arranged ahead and behind each of said depressions for holding said elastic tape.

11. The apparatus of claim 10, wherein said holding elements comprise elongated rods with suction holes in said rods and suction generating means connected to said suction holes in said elongated rods for holding said elastic tape.

12. The apparatus of claim 4, wherein said second roller means comprise a roller surface, said cutting means comprising knives in said surface and at least two tape holding members between two neighboring cutting knives.

13. The apparatus of claim 12, wherein one tape holding member of said two tape holding members is located directly adjacent the respective cutting knife while the other tape holding member is located further away from the respective cutting knife.

14. The apparatus of claim 12, wherein said tape holding members comprise suction holes.

15. The apparatus of claim 12, wherein said two tape holding members are located in front of the respective cutting knife as viewed in the rotational direction of said second roller means.

* * * * *